(12) United States Patent
Uihlein

(10) Patent No.: US 8,128,598 B2
(45) Date of Patent: Mar. 6, 2012

(54) PRESSURE CONNECTION DEVICE FOR A GUIDEWIRE UNIT

(75) Inventor: Bernhard Uihlein, Dettingen (DE)

(73) Assignee: EPflex Feinwerktechnik GmbH, Dettingen/Ems (DE)

( * ) Notice: Subject to any disclaimer, the term of this patent is extended or adjusted under 35 U.S.C. 154(b) by 232 days.

(21) Appl. No.: 12/300,604

(22) PCT Filed: May 16, 2007

(86) PCT No.: PCT/EP2007/004410
§ 371 (c)(1),
(2), (4) Date: Nov. 12, 2008

(87) PCT Pub. No.: WO2007/131799
PCT Pub. Date: Nov. 22, 2007

(65) Prior Publication Data
US 2009/0163873 A1     Jun. 25, 2009

(30) Foreign Application Priority Data
May 17, 2006   (DE) .......................... 10 2006 024 095

(51) Int. Cl.
*A61M 5/178* (2006.01)
*A61M 3/02* (2006.01)
*A61M 31/00* (2006.01)
*A61M 29/00* (2006.01)
*A61F 11/00* (2006.01)

(52) U.S. Cl. ...................... 604/164.13; 604/39; 604/510; 606/108; 606/195

(58) Field of Classification Search ................ 604/39, 604/510; 606/108, 195
See application file for complete search history.

(56) References Cited

U.S. PATENT DOCUMENTS

| | | | | |
|---|---|---|---|---|
| 4,341,218 A | * | 7/1982 | U | ................................ 606/195 |
| 4,545,367 A | | 10/1985 | Tucci | |
| 4,909,796 A | * | 3/1990 | Hagio et al. | .................. 604/247 |

(Continued)

FOREIGN PATENT DOCUMENTS

DE      698 28 985 T2    10/2005

(Continued)

OTHER PUBLICATIONS

International Search Report dated Oct. 4, 2007 w/English translation (four (4) pages).
German Search Report dated Apr. 13, 2007 w/English translation (six (6) pages).

*Primary Examiner* — Nicholas Lucchesi
*Assistant Examiner* — Ian Holloway
(74) *Attorney, Agent, or Firm* — Crowell & Moring LLP

(57) ABSTRACT

A pressure connection device for a guidewire unit that is operated with a pressure medium is provided. A return valve is mounted in the interior of a tube end section of a pressure medium tube of the guidewire unit, the return valve opening for introducing the pressure medium into the pressure medium tube and closing in order to prevent the pressure medium from escaping from the pressure medium tube, and/or a connecting body accommodates the tube end section of the pressure medium tube and has a pressure medium-controlled tube holding element which secures the tube end section to the connecting body in a fluid-tight manner when impinged upon with pressure and, in a pressure-relieved state, releases it so it can be detached from the connecting body.

10 Claims, 4 Drawing Sheets

U.S. PATENT DOCUMENTS

| | | | |
|---|---|---|---|
| 5,181,921 A * | 1/1993 | Makita et al. | 606/195 |
| 5,478,331 A * | 12/1995 | Heflin et al. | 604/537 |
| 6,527,761 B1 * | 3/2003 | Soltesz et al. | 604/516 |
| 2006/0015038 A1 | 1/2006 | Weymarn-Scharli | |
| 2008/0109028 A1 | 5/2008 | Styrc | |

FOREIGN PATENT DOCUMENTS

| | | |
|---|---|---|
| FR | 2 872 696 A1 | 1/2006 |
| WO | WO 98/48885 A1 | 11/1998 |
| WO | WO 2004/035124 A1 | 4/2004 |

* cited by examiner

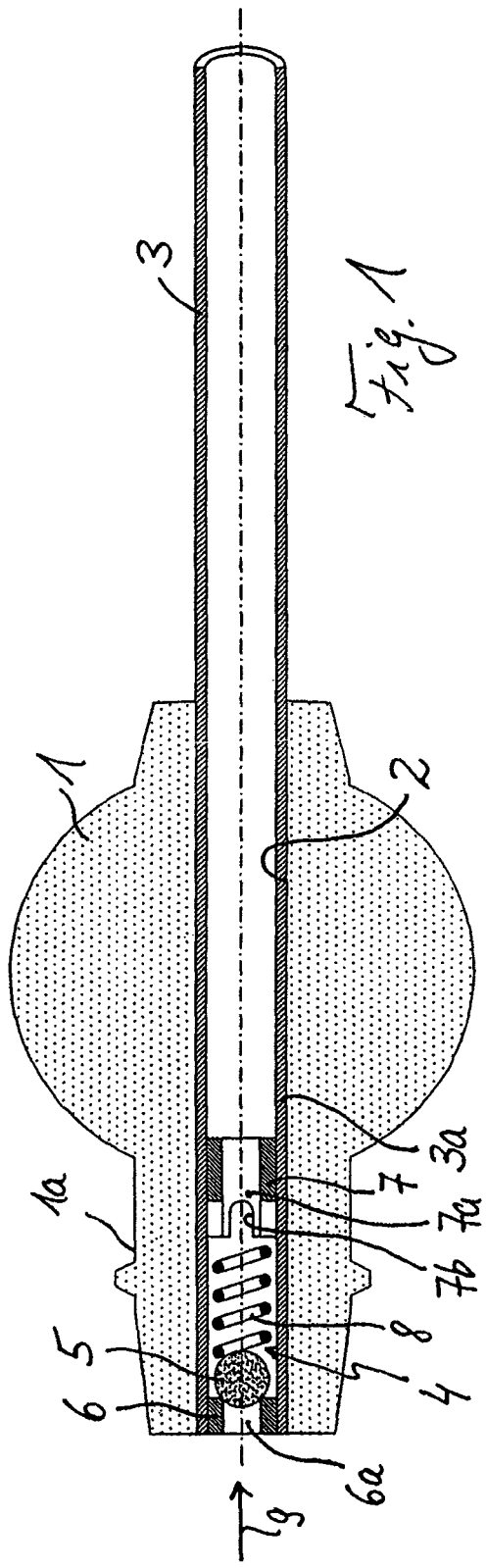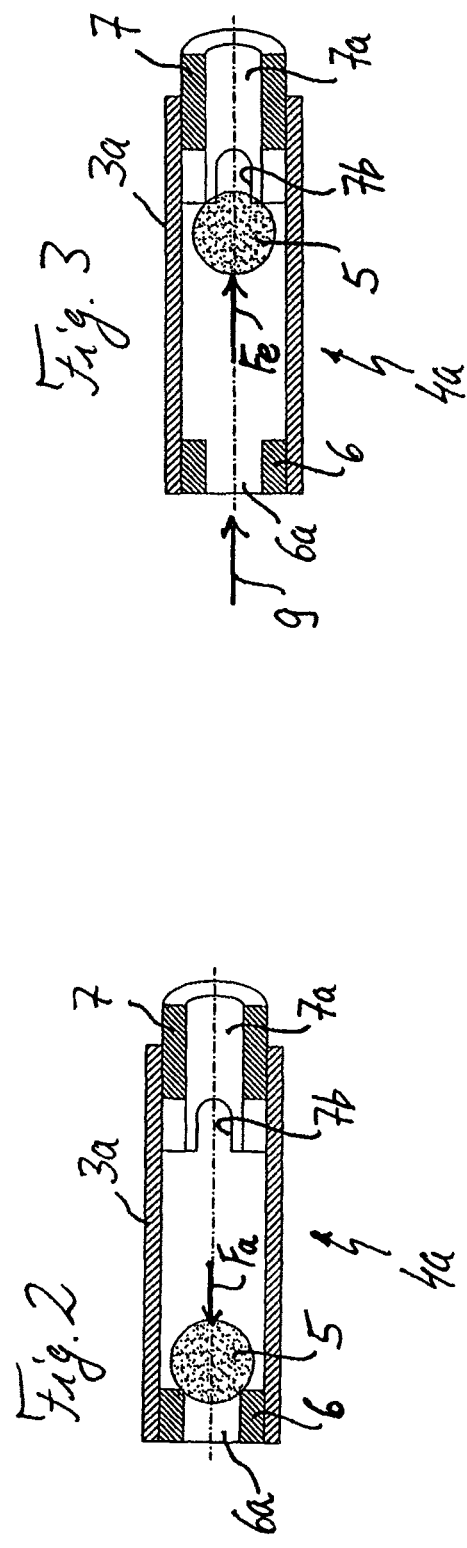

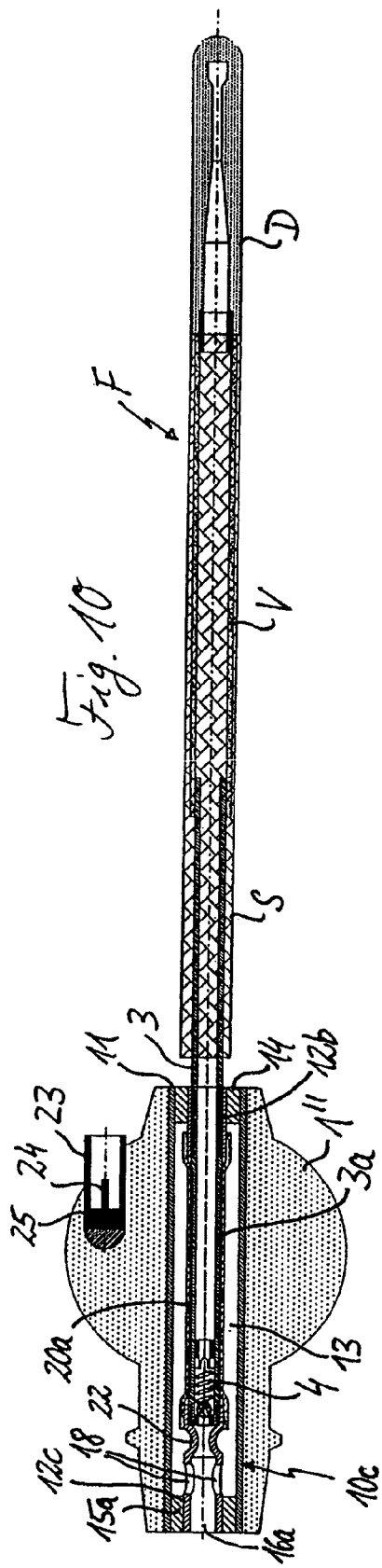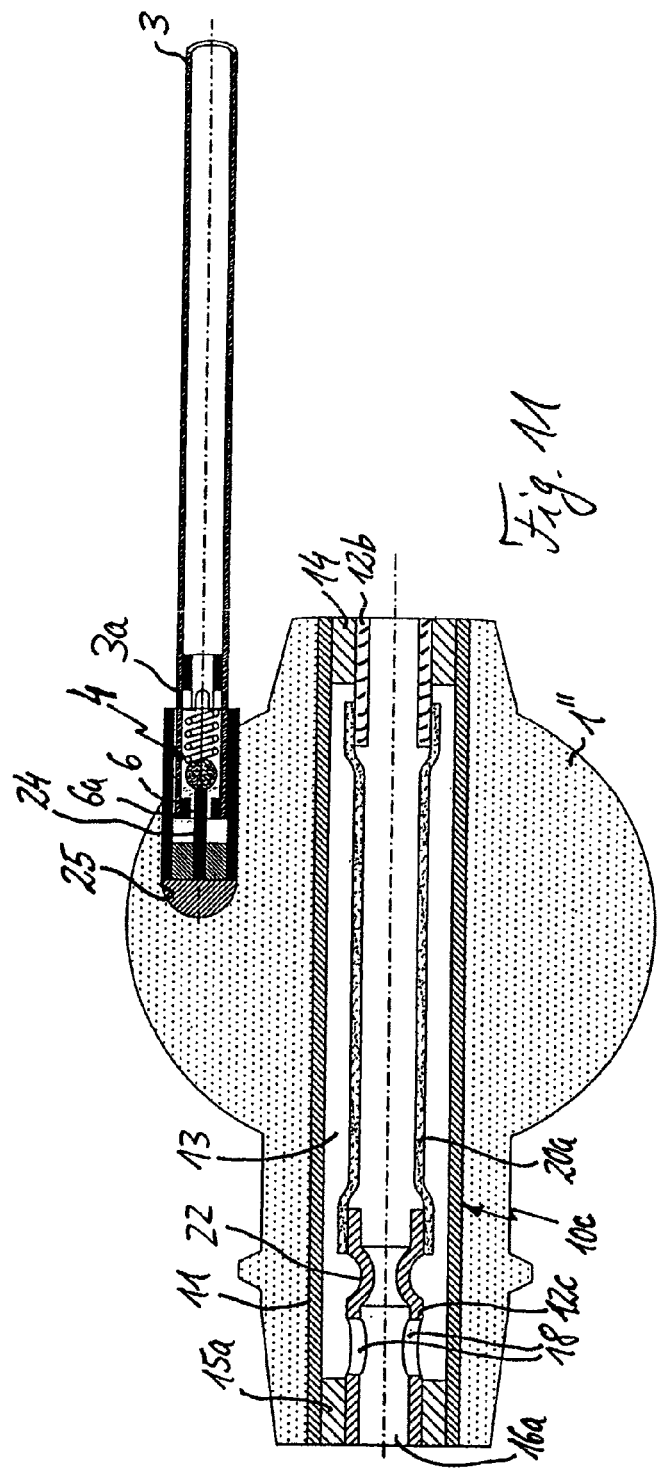

PRESSURE CONNECTION DEVICE FOR A GUIDEWIRE UNIT

CROSS-REFERENCE TO RELATED APPLICATIONS

This application contains related subject matter to co-pending application Ser. No. 12/300,615, which is a national stage of PCT International Application No. PCT/EP2007/004301, filed May 15, 2007 and designating the United States.

BACKGROUND AND SUMMARY OF THE INVENTION

The invention relates to a pressure connection device for a guidewire unit that is operated with a pressure medium. Such guidewire units are used, in particular, for medical instruments, as for example catheters in body ducts and/or tissue channels of a patient.

WO 2004/035124 A1 discloses a guidewire unit, which can be stiffened in a controlled manner and which can be put selectively into a more or less rigid state with the use of a pressure medium. Consequently, this guidewire unit needs a suitable pressure connection device for feeding the pressure medium into the guidewire unit and for discharging the pressure medium from the guidewire unit.

Especially in the field of medicine, so-called Luer lock connectors or rather Luer connectors are used to connect cannulae, syringes, infusion tubes, etc. to a supply source for a liquid or gaseous medium.

The invention is based on the technical problem of providing a pressure connection device, with which a guidewire unit of the conventional type, used for example, in medical instruments and which operates with a pressure medium, can be connected to a respective pressure medium source in an advantageous manner.

The invention solves this problem by providing a pressure connection device, which is intended for a guidewire unit operated with a pressure medium, in particular, for application in medical instruments, and which includes a connecting body, which accommodates a tube end section of a pressure medium tube of the guidewire unit. The connecting body has a pressure medium-controlled tube holding element, which in a pressurized state secures the tube end section in the connecting body in a fluid tight manner, and in a pressure relieved state releases the tube end section in order to detach from the connecting body.

The pressure connection device, comprises, in particular, a pressure medium-controlled tube holding element, which is provided on the connecting body, which accommodates a tube end section of a pressure medium tube of the guidewire unit. The tube holding element is configured so as to hold detachably the tube end section, so that in a pressurized state the tube holding element secures the tube end section in the connecting body in a fluid tight manner, and in a pressure relieved state the tube holding element releases the tube end section for removal from the connecting body. In this way, it is possible to achieve a detachable coupling of the guidewire unit, which is to be supplied with the pressure medium, to an associated pressure medium source in a manner that is advantageous from both a functional and production viewpoint. In the case under discussion, the term fluid is defined as both liquid and gaseous mediums. That is, the fluid tight seal provides protection against leaks from either liquid or gaseous pressure mediums, which are used as a function of the application.

In a further development of the invention, the tube holding element exhibits a holding/sealing diaphragm, which in the pressure relieved state allows an axial movement of the tube end section, which is accommodated in the connecting body, whereas in the pressurized state the holding/sealing diaphragm rests against the tube end in a securing and fluid tight manner. This feature constitutes a realization of the tube holding element that is advantageously simple and functionally reliable. In an advantageous embodiment of this technique, the holding/sealing diaphragm is designed as a sealing diaphragm sleeve, which in the pressure relieved state envelops the tube end section, which is accommodated in the connecting body, in such a manner that this tube end section can still perform an axial movement in and/or in relation to the sealing diaphragm sleeve. As an alternative, it is possible to design the holding/sealing diaphragm in other ways, for example, in the form of a holding diaphragm, which rests only locally against the tube end section, which is accommodated in the connecting body, without totally enveloping the tube end section in the circumferential direction.

In another embodiment of the invention, the tube holding element exhibits a pressure chamber, which can be filled with a pressure medium and on which the holding/sealing diaphragm abuts, so that the holding/sealing diaphragm can be switched between its state, in which it secures the tube end section, and its state, in which it releases the tube end section, by controlling the medium pressure in the pressure chamber.

In an advantageous further development of the invention, the tube holding element exhibits a pressure medium connecting element, which is configured in such a manner that it feeds the same pressure medium to the pressure chamber as to the pressure medium tube. Consequently, it is possible to use in a simple way the same pressure medium, for example, compressed air, which is needed in any event for the guidewire unit, in order to control the sealing diaphragm sleeve by way of the pressure chamber.

In an additional advantageous embodiment of the invention, the pressure medium connecting element exhibits a feed delay system, which is configured in such a manner that it feeds the pressure medium to the pressure medium tube so as to be delayed as compared to the pressure chamber. This feature guarantees that at an adequately early stage the sealing diaphragm sleeve already secures the tube end section in a fluid tight manner before the inlet area of the pressure medium tube exhibits a noticeable buildup in pressure owing to the delivered pressure medium. That is, the feed delay guarantees in an automatic way that at an adequately early stage the sealing diaphragm sleeve will be put into its pressurized state, which seals the accommodated tube end section, when the pressure medium is to be fed into the pressure medium tube. Thus, expensive pressure controlling mechanisms elsewhere are not absolutely necessary.

A variety of different variants may be considered in order to realize the feed delay system. Of these variants, two advantageous variants are provided as further developments of the invention. Thus, it is possible to realize the delayed feed of the pressure medium to the pressure medium tube as compared to the pressure chamber by running a pressure inlet, which can be connected to a pressure medium source, directly to the pressure chamber and by connecting an inlet area of the pressure medium tube to the pressure chamber by means of one passage aperture or a plurality of passage apertures in a corresponding partition. Therefore, the delivered pressure medium flows first and primarily into the pressure chamber and from there into the inlet area of the pressure medium tube and finally into the pressure medium tube itself, so that the sealing diaphragm sleeve has already moved with certainty into its sealing, pressurized state, before the inlet area of the pressure medium tube exhibits a buildup of any noticeable pressure of the pressure medium, which could lead to leaks in that area if the sealing diaphragm sleeve were not yet adequately pressurized. According to another variant, the delayed feed of the pressure medium to the pressure medium tube as compared to the pressure chamber is brought about by a cross section-reducing inlet nozzle, which is located downstream of a connection of the pressure medium inlet to the pressure chamber in the inlet area to the pressure medium tube. In this case, too, the pressure builds up first and primarily in the pressure chamber. As a result, the sealing diaphragm sleeve assumes its pressurized state, in which it secures the tube end section in a fluid tight manner, before any noticeable pressure has been built up in the inlet area of the pressure medium tube downstream of the inlet nozzle.

The pressure connection device comprises typically a return valve, which is mounted in the interior of the tube end section of the pressure medium tube of the guidewire unit and which opens in order to introduce the pressure medium into the pressure medium tube and closes in order to prevent the pressure medium from flowing out of the pressure medium tube. This feature automatically prevents the pressure medium from escaping from the pressure medium tube and, thus, from the guidewire unit, when the pressure medium has been fed beforehand to this guidewire unit, even if the guidewire unit with its pressure medium tube is detached from a pressure connection that is used eventually in order to connect to a corresponding pressure medium source. Mounting the return valve in the interior of the tube end section does not change the outer diameter of the respective tube end section and/or connecting area of the pressure medium tube and, thus, the guidewire unit in this area, so that the guidewire unit, which is provided with the return valve, can be used or rather can be manipulated without the return valve in the same way as an analogous conventional guidewire unit.

The technique of mounting the return valve in the tube end section of the pressure medium tube of the guidewire unit can be combined especially with the techniques with respect to attaching in a detachable manner the guidewire unit to a connecting body. In this case, the return valve makes sure that upon removal of the connecting body from a pressure medium source and/or upon removal of the guidewire unit from the connecting body, the pressure medium, which was fed beforehand into the guidewire unit, stays there.

In an advantageous embodiment of the invention, the return valve comprises a ball valve and one associated closing and opening stop each for said ball valve. Both the closing stop and the opening stop are fitted into the tube end section at an axial distance in such a manner that the ball valve can move adequately in the axial direction and in the pressurized state of the guidewire unit rests in a closing manner against the closing stop, whereas upon introduction of the pressure medium into the pressure medium tube, said ball valve leaves its closing position at the closing stop and moves in the direction of the opening stop. The opening stop exhibits a pressure medium passage aperture, which remains open even in the event that the ball valve is resting or pushing against said opening stop so that the pressure medium can flow into the pressure medium tube. In an advantageous embodiment, a return spring is braced against the opening stop. This return spring pushes the ball valve against the closing stop. Such a return spring is not absolutely mandatory, but it can facilitate the ball valve and, in addition, can control in a desired manner the feeding of the pressure medium through the choice of a suitable spring tension.

An additional embodiment of the invention provides a pressure relief pin in order to force open the return valve. To this end, the pressure relief pin exhibits an actuating mandrel, with which the ball valve can be moved away from its closing stop in the direction of the opening stop. In this way the pressure medium can be drained from the guidewire unit, and the guidewire unit can be moved into a less pressurized and/or pressure relieved state. In an advantageous embodiment, the pressure relief pin can be accommodated in a detachable or stationary manner in a receptacle of the connecting body, so that it does not have to be stored separately.

Advantageous embodiments of the invention are depicted in the drawings and are described below.

BRIEF DESCRIPTION OF THE DRAWINGS

FIG. 1 is a longitudinal sectional view of a pressure connection device including a tube end section of a pressure medium tube of a guidewire unit, the tube end section being securely accommodated in a connecting body and provided with a spring-supported return valve;

FIG. 2 is a longitudinal sectional view of an alternative return valve, as depicted in FIG. 1, but without a return spring, in the closed state;

FIG. 3 is a longitudinal sectional view of the alternative return valve of FIG. 2 in the opened state;

FIG. 10 is a longitudinal sectional view, corresponding to FIG. 9, for an alternative with a pressure relief pin, which is accommodated additionally at the connecting body, in order to actuate the return valve and a guidewire unit, which can be coupled in a detachable manner with the connecting body; and FIG. 11 is a longitudinal sectional view, corresponding to FIG. 10, but with a guidewire unit, which is detached from the connecting body and which is functionally connected to the pressure relief pin.

DETAILED DESCRIPTION OF THE DRAWINGS

Figure 4:
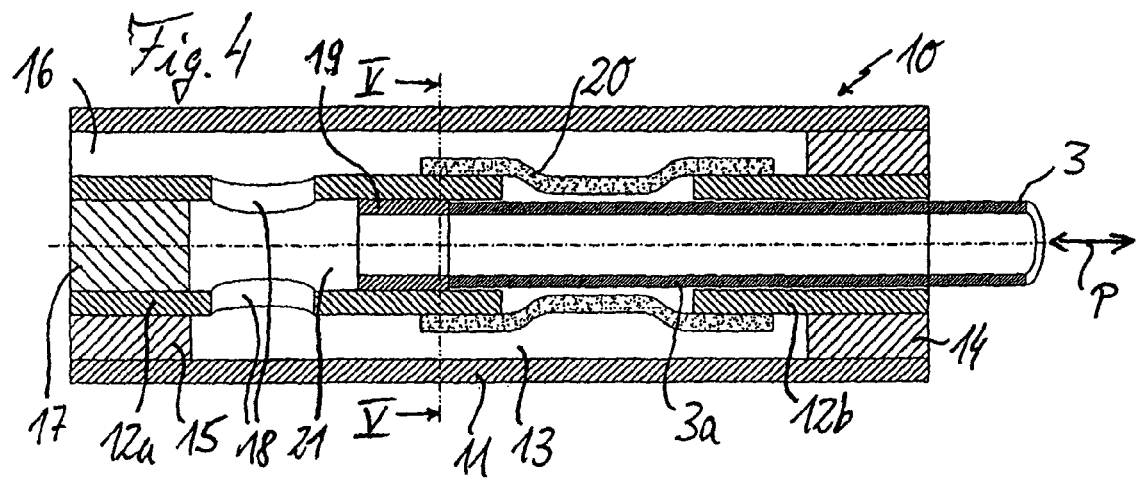
FIG. 4 is a longitudinal sectional view of a tube holding element for holding in a detachable fluid tight manner a tube end section of a pressure medium tube of a guidewire unit in a pressure relieved state.

A pressure connection device, shown in FIG. 1, includes a connecting body 1, the outer shape of which forms with an associated end connection piece 1*a* a Luer lock connection or short Luer connection. The connecting body 1 is provided with a continuous central axial borehole 2, into which is rigidly inserted a tube end section 3*a* of a pressure medium tube 3 of a guidewire unit, which is not shown here in detail.

In this case, the face side of the tube end section 3a terminates flush with the connection piece 1a of the connecting body 1.

A return valve 4 is mounted in the interior of the tube end section 3a. The return valve includes a ball valve 5, a sleeve-shaped closing stop 6 for the ball valve, an opening stop 7, which also has the shape of a sleeve, and a return spring 8. The closing stop sleeve 6 and the opening stop sleeve 7 are inserted securely and at a certain axial distance from each other into the tube end section 3a. The outside of the closing stop sleeve 6 closes axially and flush with the tube end section 3a and the connection piece 1a. The other face side of the closing stop sleeve is formed in such a manner (not shown in detail) that in the illustrated closing position of the ball valve 5, the ball valve locks a central through-flow channel 6a, which is formed in the closing stop sleeve 6. The return spring 8 is braced against the opening stop sleeve 7 and prestresses the ball valve 5 against the closing stop sleeve 6. The opening stop sleeve also has a central through-flow channel 7a and is additionally provided with axially integrated opening slots 7b on the face side facing the ball valve 5.

The illustrated pressure connection device serves to connect the guidewire unit with its pressure medium tube 3 to a pressure medium source, in order to provide, as necessary, the guidewire unit with a pressure medium. To this end, the connecting body 1 with its Luer connection piece 1a can be functionally connected to a matching connection of the pressure medium source, for example, a compressed air source. As soon as the conventional pressure medium source (hence, not illustrated here) releases the pressure medium 9 for feeding into the pressure medium tube 3, the return valve 4 opens by lifting the ball valve 5 via the pressure of the pressure medium 9 from the closing stop 6 counter to the force of the return spring 8 and moving the ball valve 5 in the direction of the opening stop 7. As a result, the pressure medium 9 flows through the through-flow aperture 6a of the closing stop sleeve 6 into the interior of the return valve 4 and from there through the passage aperture 7a of the opening stop sleeve 7 into the interior of the pressure medium tube 3, from where it continues to flow to a desired point of the guidewire unit.

After uncoupling the connecting body 1 of the guidewire unit from the pressure medium source, the return valve 4 closes, as shown in FIG. 1, by pushing the ball valve 5 against the closing stop sleeve 6 by the return spring 8 and by the pressure, generated in the interior of the pressure medium tube 3. As a result, the pressure, generated in the guidewire unit, is held even after uncoupling from the pressure medium source. For example, the pressure, generated in this manner in the guidewire unit, may serve to put an aforementioned conventional guidewire unit into a state, in which it has a higher resistance to bending than in a pressure relieved, less rigid state. Similarly, the pressure connection device for guidewire units that exhibit a section that can be stiffened in a controlled manner as is the case with the subject matter of the simultaneously filed German patent application 10 2006 024 094.4 of the applicant, is suitable in an analogous way. For this reason, the content of the German patent application is fully incorporated in its entirety by reference herein in order to avoid unnecessary repetition in the present application.

The use of the return valve 4 has the advantage that the more rigid state of the entire guidewire unit and/or of its section, which may be variably stiffened by controlling the pressure medium, is maintained, even after uncoupling the guidewire unit from the pressure medium source, so that in the more rigid state the guidewire unit may be manipulated for an additional use without being impeded by the attached pressure medium source.

The return spring 8 holds the ball valve 5 with a defined prestress force in its closing seat on the closing stop sleeve 6 and helps and/or influences correspondingly the function of the return valve 4. In many applications the return spring 8 may be dispensable, if the return valve function, provided solely by the closing stop sleeve 6, the opening stop sleeve 7 and the ball valve 5, suffices. FIGS. 2 and 3 illustrate this type of a return valve variant 4a without a return spring. Moreover, for ease of comprehension the same reference numerals as in FIG. 1 are used for the identical or functionally equivalent elements. Therefore, in this respect the above description of these elements can be referenced.

FIG. 2 shows the return valve 4a in its closed state. The pressure medium, located in the pressure medium tube and consequently also in its tube end section 3a, exerts on the ball valve 5 a pressure force Fa, which acts outwardly axially in the outwards direction and which holds the ball valve 5 against its closing seat on the closing stop sleeve 6, so that the ball valve 5 blocks the passage aperture 6a of the closing stop sleeve 6 and prevents the pressure medium, located in the pressure medium tube, from escaping.

Upon coupling to a pressure source, the inflowing pressure medium 9 exerts a pressure force Fe on the ball valve 5 in the inwards direction. As a result the ball valve 5 rises, for example, starting from the closing position in FIG. 2, from its closing seat on the closing stop sleeve 6 and moves axially inward until it comes to rest, as shown in FIG. 3, against the opening stop sleeve 7, where it reliably closes the face sided mouth of the passage aperture 7a. However, the passage slots 7b, which are introduced on the face side into the sleeve shell, remain free. Moreover, since the diameter of the ball valve is selected so as to be smaller than the inside diameter of the tube end section 3a, in this position of the ball valve the pressure medium can flow through the passage aperture 6a of the closing stop sleeve 6 into the interior of the return valve 4a and from there outwardly past the ball valve 5 and through the aperture slots 7b into the passage aperture 7a of the opening stop sleeve 7, from where it continues to flow through the passage medium tube 3 to the desired point of the guidewire unit. Otherwise the return valve variant 4a in FIGS. 2 and 3 exhibits the same properties and advantages as described above with respect to the return valve 4, which is depicted in FIG. 1 and to which reference can be made.

Whereas in the embodiments shown in FIGS. 1 to 3, the pressure medium tube 3 with its corresponding tube end section 3a is coupled stationarily, that is, undetachably, with the connecting body 1, the invention also includes the possibility of a detachable connection of the pressure medium tube and, thus, the guidewire unit in its entirety to a connecting body. A variety of embodiments of this type are explained in detail below with reference to FIGS. 4 to 11. Each of the embodiments, which are depicted in those figures, comprises a tube holding element, which operates automatically by pneumatic means, in order to hold in a detachable manner the tube end section of the pressure medium tube of the guidewire unit. Therefore, in order to control this tube holding element in a very advantageous manner, the pressure medium, which is needed in any event to feed the guidewire unit, is used, and this control is achieved solely by means of flow engineering design techniques.

Figure 5:
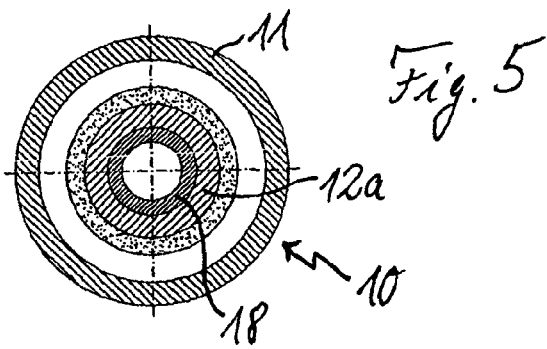
FIG. 5 is a cross sectional view along the line V-V of FIG. 4.
Figure 6:
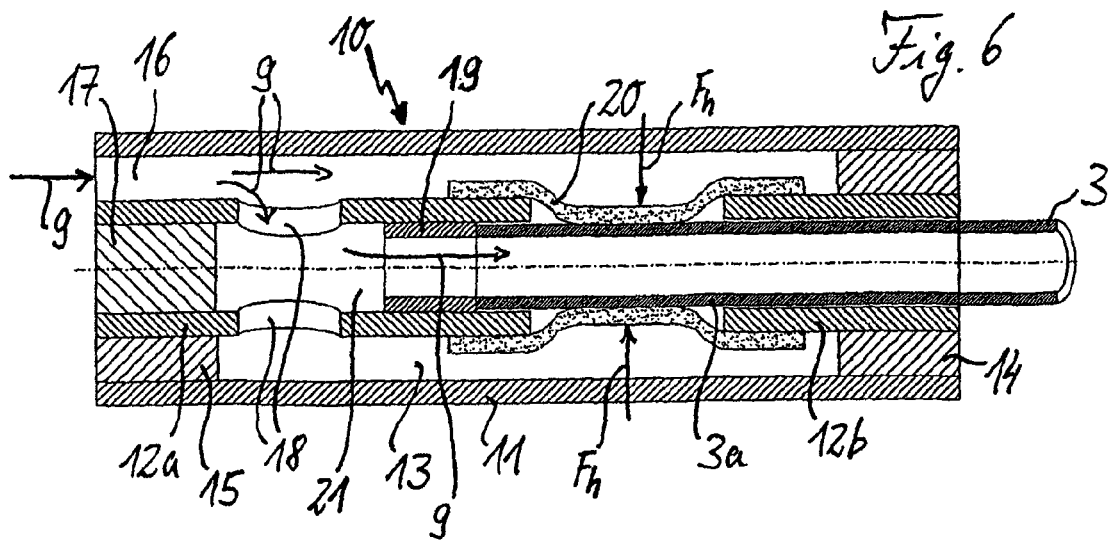
FIG. 6 is a longitudinal sectional view of a tube holding element of FIG. 4 in a pressurized state.

FIGS. 4 to 6 depict a first embodiment of such a tube holding element 10 for holding in a detachable manner the tube end section 3a of the pressure medium tube 3 of a coupled guidewire unit, which is not shown in detail. The tube holding element 10 includes an outer sleeve 11 and a two-part inner sleeve with an axially exterior sleeve component 12a and an axially interior sleeve component 12b, both of which have the same diameter and are arranged at a specifiable axial distance from each other. The interior sleeve components 12a, 12b have an outside diameter that is less than the inside diameter of the outer sleeve 11 and are inserted into the outer sleeve 11 while simultaneously leaving an annular pressure chamber 13. The axially inner interior sleeve component 12b is held in the outer sleeve 11 by way of a ring seal 14, which seals in a fluid tight manner the annular pressure chamber 13 on its respective face side.

The axially outer interior sleeve component 12a is also held in the outer sleeve 11 on the other face side by way of a ring seal 15. However, this ring seal 15 exhibits at least one axial passage aperture 16, which acts as the pressure medium inlet port.

In the radially inwards direction the interior sleeve component 12a is sealed in a fluid tight manner on its outer face side by a stopper 17. In an area adjacent to the stopper 17 in the axially inward direction, the axially outer interior sleeve component 12a is provided with a plurality of passage apertures 18, which are distributed in the circumferential direction, in its shell. In an area, which is adjacent thereto in the axially outward direction, the axially outer interior sleeve component 12a accommodates a securely inserted tube stop sleeve 19, which matches in its diameter and tube wall thickness approximately the tube end section 3a, which is to be accommodated and which is part of the pressure medium tube 3 of the guidewire unit. Thus, the tube stop sleeve 19 serves as a stop, against which the face side of the tube end section 3a comes to rest upon insertion into the tube holding element 10.

The tube holding element 10 exhibits a sleeve-shaped, flexible, expandable sealing diaphragm 20 as the active tube holding element. The sealing diaphragm bridges the axial intermediate space between the axially outer interior sleeve component 12a and the axially inner interior sleeve component 12b and is held on the face side so as to be slipped over, that is, by shrinking on, the axially outer interior sleeve components 12a and/or the axially inner interior sleeve component 12b. The axially outer and the axially inner interior sleeve components 12a, 12b act in this way as the sealing diaphragm holding elements.

The tube holding element 10, which is constructed as described above, functions as follows. In the pressure relieved state the tube holding element 10 is in a state (as shown in FIG. 4), which releases the accommodated tube end section 3a. In the gap between the axially outer and the axial inner interior sleeve components 12a, 12b, the sealing diaphragm 20 rests just loosely against the accommodated tube end section 3a or maintains a certain radial distance from the tube end section. As a result, the pressure medium tube 3 with its tube end section 3a can be pulled out of the tube holding element 10 in the axial direction and can be inserted again, as necessary, into the tube holding element as far as up to the tube stop sleeve 19, a feature which is symbolized with a double arrow P in FIG. 4. As an alternative, the system may also be configured in such a way that the sealing diaphragm sleeve 20 is designed somewhat narrower than the outside diameter of the tube end section 3a and rests, therefore, flush against the inserted tube end section 3a as early as in the pressure relieved state. However, the ability to move the tube end section 3a axially in relation to the enveloping sealing diaphragm sleeve remains guaranteed.

Upon coupling the tube holding element 10 with its inlet 16 to a pressure medium source (not illustrated), the pressure medium 9 flows through the inlet 16 first and primarily into the annular pressure chamber 13, which is connected directly to the inlet 16. As a result, the pressure builds up very quickly in the annular pressure chamber 13. This pressure exerts a radially inwards acting pressure force Fh on the flexible, expandable sealing diaphragm 20. Hence, the sealing diaphragm 20 is pushed, securely and in the circumferential direction closed, against the outside of the tube end section 3a, a feature that is shown in FIG. 6. As a result, the pressure medium tube 3 with its tube end section 3a is held rigidly and in a fluid tight manner in the tube holding element 10. Then the pressure medium 9 continues to flow through the radial passage apertures 18 in the axially outer interior sleeve component 12a into its interior, which acts as the inlet area 21 for the pressure medium tube 3, from where the pressure medium 9 continues to flow through the stop sleeve 19 into the pressure medium tube 3.

The aforementioned flow engineering design of the tube holding element 10 has the effect without any additional control measures that the pressure medium tube 3 is held in an adequately secure and fluid tight manner by the sealing/holding diaphragm 20, before any noticeable pressure of the pressure medium 9 has built up in the inlet area 21 and in the pressure medium tube 3.

As a result, the sealing/holding diaphragm 20 prevents at a sufficiently early stage a pressure-induced axial migration of the pressure medium tube 3 from the tube holding element 10 and an undesired escape of the pressure medium 9 due to some leak between the tube stop sleeve 19 and the tube end section 3a as well as between the interior sleeve components 12a, 12b and the sealing diaphragm 20, on the one hand, and the tube end section 3a, on the other hand. Since the outside of the tube end section 3a is sealed by the sealing diaphragm 20 in the medium inflow direction upstream of the axially inner interior sleeve component 12b, there is no need for additional sealing measures in the area between the tube end section 3a and the surrounding interior sleeve component 12b.

After uncoupling the retaining element 10 from the pressure medium source, the retaining element 10 can be moved again, according to FIG. 4, into its pressure relieved state, which releases the inserted tube end section 3a, when the pressure medium 9 is allowed to escape by way of the inlet port 16.

Figure 7:
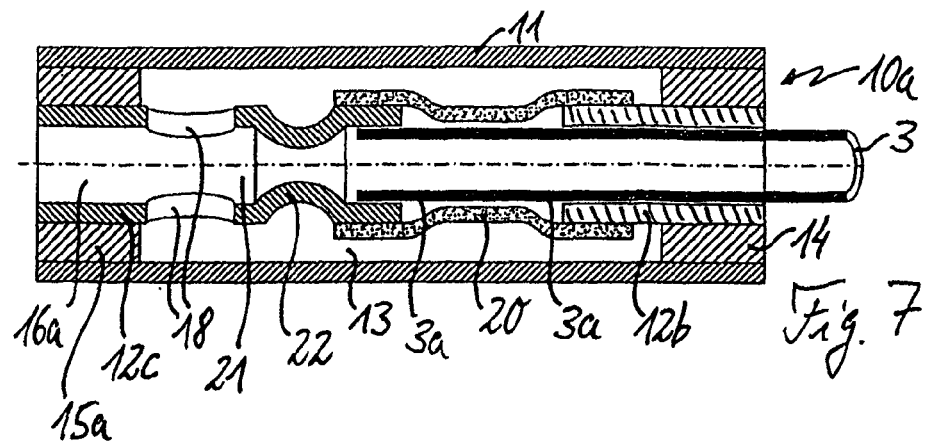
FIG. 7 is a longitudinal sectional view, corresponding to FIG. 4, for an alternative of the tube holding element with a cross section-reducing inlet nozzle, which is molded on a sealing diaphragm holding component.
Figure 8:
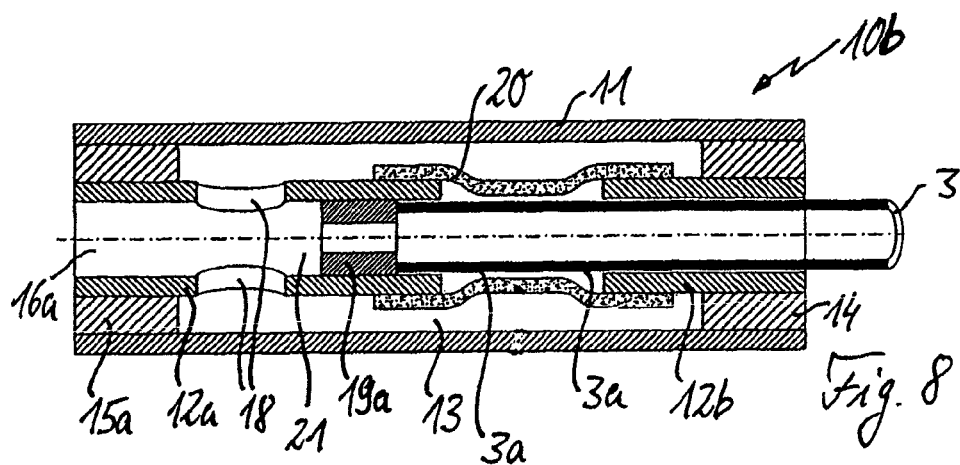
FIG. 8 is a longitudinal sectional view, corresponding to FIG. 7, for an alternative with a cross section-reducing inlet nozzle, which is installed separately.

FIGS. 7 and 8 depict the design variants of the flow engineering configuration that guarantee that at a sufficiently early stage the inserted tube end section 3a of the pressure medium tube of the guidewire unit will be held in a fluid tight manner in the same way as described with reference to the embodiment, shown in FIGS. 4 to 6. Once again the same reference numerals are selected for the identical or functionally equivalent elements. Hence, in this respect reference can be made to the above description of FIGS. 4 to 6.

In particular, FIG. 7 depicts a tube holding element 10a, which exhibits the following differences with respect to the tube holding element in FIGS. 4 to 6. In this example, a central aperture 16a of an axially outer interior sleeve component 12c acts as the inlet port. In comparison to the interior sleeve component shown in FIGS. 4 to 6, this interior sleeve component is additionally modified in that in an axially inner section, adjoining the area provided with the radial passage apertures 18, the interior sleeve component is formed with a constriction, which acts as a cross section-reducing inlet nozzle 22 on the downstream end of the inlet area 21. The axially outer interior sleeve component 12c is held on the outer sleeve 11 by a ring seal 15a, which is closed on the reverse side. As a result, the annular pressure chamber 13 is also sealed outwardly on the face side. At the same time the cross section-reducing inlet nozzle 22 is used, instead of the tube stop sleeve 19 in FIGS. 4 to 6, as the limit stop for the inserted tube end section 3a.

Therefore, in the case of the tube holding element 10a in FIG. 7, upon coupling to a pressure medium source, the pressure medium flows then through the central inlet 16a into the inlet area 21 and from there, owing to the relatively large radial passage apertures 18, very quickly into the annular pressure chamber 13, so that the necessary pressure is generated correspondingly quickly in said annular pressure chamber, in order to push the sealing/holding diaphragm 20 securely in the radial inwards direction and in a fluid tight manner against the tube end section 3a. In contrast, the pressure buildup in the tube end section 3a is delayed by the action of the cross section-reducing inlet nozzle 22. Hence, once again without any additional control-related measures the effect is achieved even in the case of a tube holding element 10a of FIG. 7 that just the flow engineering design techniques alone generate first and primarily the pressure that is required for activating the sealing/holding diaphragm 20 in the annular pressure chamber 13, before any noticeable pressure builds up in the tube end section 3a. In the event that the sealing diaphragm 20 has not achieved a seal yet, this pressure could lead to an undesired migration of the pressure medium tube 3 out of the tube holding element 10a and/or to an undesired leak in the area between the tube end section 3a, on the one hand, and its surrounding areas of the axially outer interior sleeve component 12c, the sealing diaphragm 20 and the axially inner interior sleeve component 12b, on the other hand.

The same effect is also achieved in the case of a tube holding element 10b, according to FIG. 8. The distinction between this tube holding element and that in FIG. 7 lies only in the use of the axially outer interior sleeve component 12a of the example in FIGS. 4 to 6 and, instead of the inlet nozzle 22, which is molded on the axially outer interior sleeve component itself and is part of the example in FIG. 7, the use of a modified tube stop sleeve 19a. This tube stop sleeve 19a matches in shape and function the tube stop sleeve 19 of the example in FIGS. 4 to 6, with the exception that its inside diameter is chosen so as to be significantly smaller than the inside diameter of the tube end section 3a, so that this tube stop sleeve 19a acts not only as the limit stop for the inserted tube end section 3a but also simultaneously as the cross section-reducing inlet nozzle. Thus, even in the case of the tube holding element 10b of FIG. 8, upon coupling to a pressure medium source, the pressure builds up first and primarily in the annular pressure chamber 13. As a result, the sealing/holding diaphragm 20 holds securely in a fluid tight manner the inserted tube end section 3a, before any noticeably pressure builds up then in the tube end section 3a.

In other embodiments of the invention that are not illustrated in detail here, the sealing/holding diaphragm for the tube holding element is designed in such a manner that it does not fully envelop the tube end section, accommodated in the connecting body, in the circumferential direction, as is the case for a design as a sealing diaphragm sleeve, but rather rests against the tube end section only locally along a periphery-sided subsection, for example, as a shell-shaped or arc-shaped holding diaphragm. This feature is suitable especially in application cases, in which the holding diaphragm does not have to fulfill, besides its pressurized, triggerable holding function, any additional sealing function, because the chosen configuration alleviates the need for such a sealing function or because the sealing function is provided by a different sealing element.

In an additional variant the sealing/holding diaphragm is designed as a sealing ring lip, which is put only on one of the two interior sleeve components, preferably on the axially outer interior sleeve component 12b, and extends with its free lip end into the intermediate space between the two interior sleeve components, so that the tube end section 3a can be inserted through the free sealing lip end as far as up to the axially inner interior sleeve component 12a. Preferably the inside diameter of the free sealing lip end is chosen so as to be less than the outside diameter of the tube end section 3a, so that in the pressure relieved state the sealing lip is already resting flush with the inserted tube end section 3a. As a result, the ability of the tube end section to move axially in relation to the enveloping sealing lip remains preserved as long as the sealing lip is not put into the pressurized state.

Figure 9:
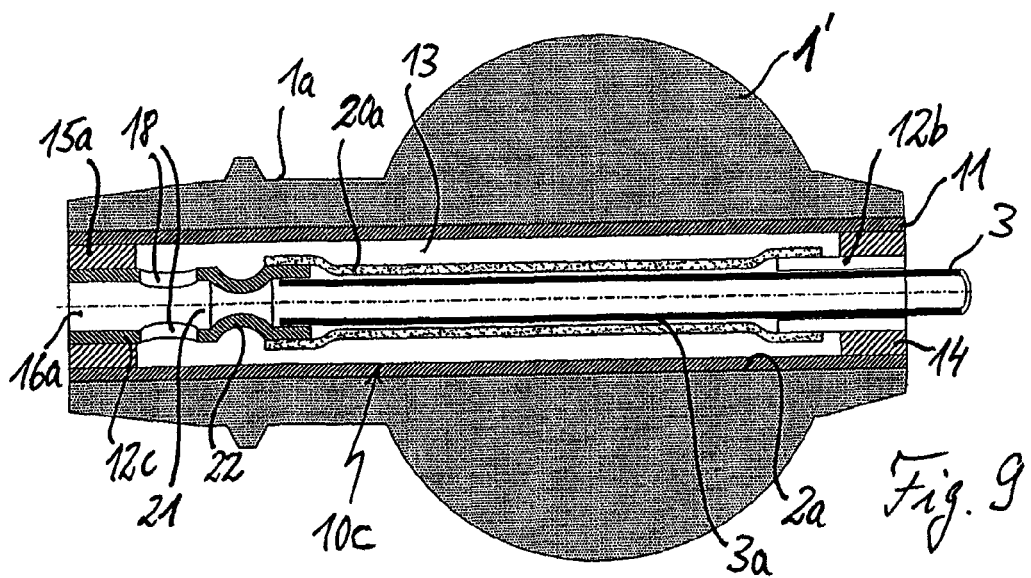
FIG. 9 is a longitudinal sectional view of a connecting body with an integrated tube holding element of the type in FIG. 7 and a tube end section of a pressure medium tube of a guidewire unit, said tube end section being accommodated in a detachable manner in said tube holding element.

The tube holding element, which has been described above with respect to various variants, can be used, in particular, to connect in a detachable manner the pressure medium tube of a guidewire unit with its corresponding tube end section to a connecting body in order to attach to a pressure medium source. FIG. 9 shows a corresponding variant of the embodiment in FIG. 1, where the guidewire unit with its pressure medium tube 3 is held detachably in a connecting body 1' with the use of a tube holding element 10c. The external shape of this connecting body matches that of the connecting body shown in FIG. 1. At this point it must be mentioned that the connecting body 1' and the corresponding components of the tube holding element 10c, like the outer sleeve 11 and the interior sleeve components 12b, 12c, can be manufactured as injection molded parts.

The tube holding element 10c, which is used in FIG. 9, matches that in FIG. 7 with the single exception that a greater axial distance between the axially outer interior sleeve component 12c and the axially inner interior sleeve component 12b and a matching sealing/holding diaphragm 20a with a correspondingly longer axial length is provided. The sealing diaphragm sleeve 20a is somewhat narrower than the outside diameter of the tube end section 3a of the pressure medium tube 3 and, therefore, rests against this tube end section as early as in the pressure relieved state. However, the sealing diaphragm sleeve allows axial movements of the tube end section 3a. The tube holding element 10c is securely inserted with its outer sleeve 11 so as to fit accurately into a corresponding axial central borehole 2a of the connecting body 1'. The inlet port 16a of the tube holding element 10c forms simultaneously the inlet port of the pressure connection device, which is formed in this way, in order to couple with a pressure medium source, for example, using Luer lock technology.

In the pressure relieved state of the pressure connection device in FIG. 9, the connecting body 1' can be removed together with the integrated tube holding element 10c axially from the pressure medium tube 3 and/or the latter can be pulled axially out of the connecting body 1' with the integrated tube holding element 10c, because the sealing/holding diaphragm 20a releases the tube end section 3a, which is surrounded by said sealing/holding diaphragm, for this purpose. When the pressure connection device with its inlet 16a is attached to a pressure medium source, the pressure medium flows into the inlet area 21 and from there primarily into the annular pressure chamber 13. As a result, the sealing/holding diaphragm 20a is activated correspondingly quickly, that is, is securely pressed radially inwards against the tube end section 3a and holds it securely in a fluid tight manner. In the next sequence of events the pressure medium flows through the cross section-reducing inlet nozzle 22 into the pressure medium tube 3, where it continues to flow to the desired point of the guidewire unit.

After uncoupling from the pressure medium source, the inlet 16 can be closed, as required, for example, with a stopper, when the pressure is supposed to be held in the pressure medium tube 3, and the connecting body 1' is supposed to remain on the tube end section 3a of the pressure medium tube 3. As an alternative, the pressure may be released in its entirety, so that the pressure connection device assumes again its pressure relieved state (shown in FIG. 9), in which the connecting body 1' with the integrated tube holding element 10c can be detached from the pressure medium tube 3. When the pressure is supposed to be held in the pressure medium tube 3, this pressure medium tube can be closed on the face side, for example, with a stopper. As an alternative, the tube end section 3a can be equipped with a return valve in accordance with FIGS. 1 and 3.

A respective embodiment is depicted in FIGS. 10 and 11.

FIG. 10 depicts a guidewire unit F, which is held detachably with the tube end section 3a of its pressure medium tube 3 in a connecting body 1", which matches in essence that in FIG. 9 and is integrated especially in the tube holding element 10c. In the guidewire unit F of FIG. 10, the return valve 4, according to the example in FIG. 1, is mounted on the tube end section 3a, which is accommodated in the connecting body 1". Following the tube end section 3a, the guidewire unit F exhibits in succession a stiff section S, through which extends the pressure medium tube 3, a variable section V, which can be set variably between at least two different bending resistances so as to control its stiffness by use of the introduced pressure medium, and a distal terminating section D. For more information about the detailed construction and the operating principle of this guidewire unit F, reference can be made to the applicant's parallel German patent application 10 2006 024 094.4, which shows the identical arrangement in FIG. 13 of the application.

Upon coupling with a pressure medium source, the pressure connection in FIG. 10 behaves in a manner analogous to the pressure connection in FIG. 9, so that in this respect reference can be made to the above description. In addition, there is the function of the return valve 4, which opens automatically as soon as adequate pressure has built up downstream of the cross section-reducing inlet nozzle 22. Upon uncoupling from the pressure medium source, the return valve 4 prevents the pressure medium from escaping from the pressure medium tube 3, so that the pressure medium remains in the guidewire unit F, and, consequently its variable section V continues to exhibit a correspondingly more rigid state. In contrast, the pressure medium can flow out of the annular pressure chamber 13 of the tube holding element 10c over the passage apertures 18 and the inlet port 16a, as a result of which the sealing/holding diaphragm 20a moves into its pressure relieved state. Therefore, the connecting body 1" with the integrated tube holding element 10c can be pulled axially off of the tube end section 3a of the pressure medium tube 3. In other words, the pressure connection device comprising a connecting body 1" and an integrated tube holding element 10c can be detached from the guidewire unit F, so that the guidewire unit F retains its pressurized, more rigid state.

When the guidewire unit F is to be moved back again into a less rigid state having less stiffness, that is, in a pressure relieved state, the return valve 4 is forced opened, in order to allow the pressure medium to escape from the pressure medium tube 3. To this end, there is a cylindrical pressure relief pin 23, which exhibits a central actuating mandrel 24, as is evident from FIGS. 10 and 11. The pressure relief pin 23 is accommodated in a corresponding receiving aperture 25 of the connecting body 1". Said pressure relief pin may be fitted stationarily or detachably into said receiving aperture as a function of the requirement. In any case, therefore, it is stored in a quasi loss-proof manner at the site of utilization.

When the return valve 4 is to be forced open, the guidewire unit F with its respective tube end section 3a is pushed into the cylindrical part of the actuating pin 23 as far as until the central actuating mandrel 24 has traversed the passage aperture 6a in the closing stop sleeve 6 of the return valve 4 and pushes the ball valve 5 away from its closing seat against the prestress force of the return spring 8. In order to allow the pressure medium to escape, the actuating mandrel 24 exhibits an outside diameter that is adequately less than the inside diameter of the closing stop sleeve 6. Correspondingly the design of the cylindrical section of the pressure relief pin 23 makes sure that the pressure medium, emerging from the pressure medium tube 3, can escape outwards. FIG. 11 shows the pressure medium tube 3 in its associated active position with the tube end section 3a, inserted into the pressure relief pin 23, when the pressure relief pin 23 stays in its receptacle 25 on the connecting body 1". As an alternative, it can be provided that the pressure relief pin 23 can be pulled out of its receptacle 25 and then slid over the tube end section, which is provided with the return valve 4 and is part of the pressure medium tube 3.

As the above description of the various embodiments makes clear, the inventive pressure connection device offers significant functional advantages in that it eliminates the need for major dimensional changes or other modifications of the guidewire unit itself and in that it allows, as a function of the requirement, in a structurally simple way that even after uncoupling from the pressure medium source, the pressure medium can be held in the guidewire unit and/or the guidewire unit can be coupled detachably with a connecting body. As a consequence, it is possible to detach, in particular, even while simultaneously retaining a pressurized state of the guidewire unit. It is self-evident that the inventive pressure connection device can be used for any guidewire unit, which is to be supplied with a gaseous or liquid pressure medium, in medical and non-medical applications. At the same time, the invention comprises not only the illustrated, but also numerous other possible realizations, for example, those that use a pressure medium other than the gaseous or liquid pressure medium with which the guide unit operates, in order to control the tube holding element.

The invention claimed is:

1. A system comprising:
    a guidewire unit that includes
        a pressure medium tube; and
        a return valve mounted in an interior of a tube end section of the pressure medium tube of the guidewire unit,
        wherein the return valve is operatively configured so that it opens in order to introduce a pressure medium into the pressure medium tube and closes in order to prevent the pressure medium from flowing out of the pressure medium tube;
    a pressure connection device with a connecting body operatively configured to accommodate the tube end section of the pressure medium tube of the guidewire unit,
        wherein the connecting body has a pressure medium-controlled tube holding element, which is operatively configured such that in a pressurized state the pressure medium-controlled tube holding element secures the tube end section in the connecting body in a fluid-tight manner, and in a pressure relieved state the pressure medium-controlled tube holding element releases the tube end section for detachment from the connecting body.

2. The system as claimed in claim 1, wherein the tube holding element includes a holding/sealing diaphragm arranged in the connecting body, which in the pressurized state rests in a fluid tight manner against the tube end section accommodated in the connecting body, whereas in the pressure relieved state the holding/sealing diaphragm allows the tube end section to move axially.

3. The system as claimed in claim 2, wherein the holding/sealing diaphragm is a sealing diaphragm sleeve, which envelops the tube end section.

4. The system as claimed in claim 2, wherein the tube holding element has a pressure chamber, which is fillable with a pressure medium and on which the holding/sealing diaphragm abuts.

5. The system as claimed in claim 3, wherein the tube holding element has a pressure chamber, which is fillable with a pressure medium and on which the holding/sealing diaphragm abuts.

6. The system as claimed in claim 4, further comprising a pressure medium connecting element, which is configured so as to feed to the pressure chamber the same pressure medium as to the pressure medium tube, said pressure medium being deliverable by way of a pressure medium inlet.

7. The system as claimed in claim 6, wherein the pressure medium connecting element has a feed delay system, which feeds the pressure medium to the pressure medium tube so as to be delayed as compared to the pressure chamber.

8. The system as claimed in claim 7, wherein the feed delay system comprises a direct connection of the pressure medium inlet to the pressure chamber and one or more passage apertures from the pressure chamber to an inlet area for the pressure medium tube.

9. The system as claimed in claim 7, wherein the feed delay system comprises a cross section-reducing inlet nozzle in an inlet area of the pressure medium tube and upstream thereof a connection of the pressure medium inlet with the pressure chamber.

10. The system as claimed in claim 8, wherein the feed delay system comprises a cross section-reducing inlet nozzle in an inlet area of the pressure medium tube and upstream thereof a connection of the pressure medium inlet with the pressure chamber.

* * * * *